United States Patent [19]

Mason

[11] Patent Number: 5,488,187
[45] Date of Patent: Jan. 30, 1996

[54] PROCESS FOR THE PRODUCTION OF DINITROBENZENE AND MONONITROBENZENE

[75] Inventor: Robert W. Mason, Lake Charles, La.

[73] Assignee: Olin Corporation, Cheshire, Conn.

[21] Appl. No.: 290,575

[22] Filed: Aug. 15, 1994

Related U.S. Application Data

[63] Continuation-in-part of Ser. No. 108,035, Aug. 17, 1993, Pat. No. 5,354,924, which is a continuation-in-part of Ser. No. 210,549, Jun. 22, 1988, abandoned.

[51] Int. Cl.$^6$ .................................................. C07C 205/06
[52] U.S. Cl. ................................... 568/932; 568/939
[58] Field of Search ................................. 568/932, 934, 568/939

[56] References Cited

U.S. PATENT DOCUMENTS

| | | | |
|---|---|---|---|
| 2,362,743 | 11/1944 | Crater | 568/934 |
| 2,435,544 | 2/1948 | Kokatnur | 568/929 |
| 2,739,174 | 3/1956 | Ross | 568/939 |
| 2,864,871 | 12/1958 | Morningstar | 568/932 |
| 3,293,310 | 12/1966 | Picard et al. | 568/935 |
| 3,434,802 | 3/1969 | Toischer et al. | 568/927 X |
| 3,780,116 | 12/1973 | Sahgal | 568/939 X |
| 3,928,395 | 12/1975 | Seha et al. | 568/937 X |
| 3,976,704 | 8/1976 | Vaughary | 568/939 |
| 4,028,425 | 6/1977 | Gilbert | 568/934 |
| 4,064,147 | 12/1977 | Thelen et al. | 568/937 |
| 4,112,005 | 9/1978 | Thiem et al. | 568/929 |
| 4,123,466 | 10/1978 | Lin et al. | 568/939 |
| 4,261,908 | 4/1981 | Schroeder et al. | 568/931 X |
| 4,347,389 | 8/1982 | Schumacher et al. | 568/937 |
| 4,415,744 | 11/1983 | Schumacher et al. | 568/937 X |
| 4,418,230 | 11/1983 | Bakke et al. | 568/940 |
| 4,426,543 | 1/1984 | Schumacher | 568/940 |
| 4,465,876 | 8/1984 | Milligan | 568/940 |
| 4,469,904 | 9/1984 | Wang et al. | 568/948 |
| 4,551,568 | 11/1985 | Sato et al. | 568/939 |
| 4,600,702 | 7/1986 | Schumacher | 568/927 X |
| 4,618,733 | 10/1986 | Schumacher | 568/927 |
| 4,621,157 | 11/1986 | McDaniel | 564/411 |
| 4,628,131 | 12/1986 | Schumacher | 568/937 |
| 4,935,557 | 6/1990 | Carr et al. | 568/934 |
| 5,057,632 | 10/1991 | Imm et al. | 568/934 |

*Primary Examiner*—Gary Geist
*Assistant Examiner*—Valerie Fee
*Attorney, Agent, or Firm*—Dale L. Carlson

[57] ABSTRACT

Aromatic nitration reactions and, more specifically, a process for nitrating benzene to produce dinitrobenzene or mononitrobenzene in the absence of sulfuric acid and in the absence of any dipolar aprotic solvent.

12 Claims, No Drawings

PROCESS FOR THE PRODUCTION OF DINITROBENZENE AND MONONITROBENZENE

This application is a continuation-in-part of U.S. Ser. No. 08/108,035, filed on Aug. 17, 1993, now pending, which is a continuation-in-part of U.S. Ser. No. 07/210,549, filed on Jun. 22, 1988, now abandoned.

FIELD OF THE INVENTION

This invention relates generally to aromatic nitration reactions and, more specifically, to a process for nitrating benzene to mononitrobenzene or dinitrobenzene.

BACKGROUND OF THE INVENTION

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition; the use of sulfuric acid tends to result in significant nitrocreosol and cyanide by-product formation which requires expensive waste-water treatment to remove.

In view of these disadvantages associated with mixed nitric/sulfuric acid systems, there have been recent attempts to perform gas phase or liquid phase nitrations in concentrated nitric acid in the absence of sulfuric acid. By way of illustration, U.S. Pat. No. 4,064,147 discloses the preparation of aromatic mononitro compounds (such as mononitrobenzene) by a liquid phase reaction with nitric acid having an acid concentration of between 70 percent and 100 percent by weight using a reaction temperature of between 0° C. and 80° C. When employing a relatively reactive compound such as benzene or toluene as a starting material, this patent teaches that a nitric acid concentration of between 70 and 90 percent by weight is preferred. The disclosure of this patent requires a ratio of nitric acid plus water to organic components of not below 3 when using 70 percent nitric acid, and not below 8 when using 100 percent nitric acid.

As another illustration, U.S. Pat. No. 3,928,395 discloses the use of concentrated nitric acid to nitrate aromatic compounds optionally in the presence of a dipolar aprotic solvent that is inert towards the nitrating agent. The patent requires that reaction be halted by diluting the resulting mixture with a dipolar aprotic solvent after the desired degree of nitration has been reached. Unfortunately, the use of such solvents either throughout the reaction or to halt the reaction tends to cause environmental waste disposal problems and waste stream handling problems.

Since mononitrobenzene and dinitrobenzene are useful as intermediate chemicals, new processes for the selective manufacture of these intermediates while avoiding the above-mentioned problems would be highly desirable to the polyisocyanate manufacturing community.

SUMMARY OF THE INVENTION

In one aspect, the present invention relates to a process for nitrating benzene to produce dinitrobenzene by a liquid phase nitration reaction of anhydrous nitric acid with benzene in a reactor at a reaction temperature of between 30° C. and 70° C., and a reaction pressure not exceeding atmospheric pressure, for a reaction time that is preferably less than two (more preferably less than one) hours, said reaction employing a molar ratio of nitric acid plus any water to benzene of between 15:1 and 25:1, said reaction being conducted in the absence of sulfuric acid, and in the absence of any aprotic dipolar solvent during the reaction and in the absence of any aprotic dipolar solvent to halt the reaction, to produce said dinitrobenzene in a product mixture, followed by vacuum distillation of the product mixture, in the absence of any aprotic dipolar solvent, to remove unreacted nitric acid from said product mixture thereby providing a dinitrobenzene product.

In another aspect, the present invention relates to a process for nitrating benzene to produce mononitrobenzene by a liquid phase nitration reaction of anhydrous nitric acid with benzene in a reactor at a reaction temperature of between 0° C. and 60° C., and a reaction pressure not exceeding atmospheric pressure, for a reaction time that is preferably less than 15 (more preferably less than 5) minutes, said reaction employing a molar ratio of nitric acid plus any water to benzene of between 2:1 and 4:1, said reacion being conducted in the absence of sulfuric acid, and in the absence of any aprotic dipolar solvent during the reaction and in the absence of any aprotic dipolar solvent to halt the reaction, to produce said mononitrobenzene in a product mixture, followed by vacuum distillation of the product mixture, in the absence of any aprotic dipolar solvent, to remove unreacted nitric acid from said product mixture thereby providing a mononitrobenzene product.

These and other aspects of the present invention will become apparent upon reading the following detailed description of the invention.

DETAILED DESCRIPTION OF THE INVENTION

In accordance with the process of the present invention, the nitration reaction is conducted using anhydrous nitric acid in the absence of sulfuric acid. As used herein, the term "anhydrous nitric acid" is intended to designate nitric acid having an acid concentration of between 95 and 100 weight percent, preferably at least 98 weight percent, the remainder being water. It is desirable to minimize the amount of water in the reaction mixture since water tends to prevent the nitration of benzene to mononitrobenzene.

The process of the present invention utilizes a one-step reaction in a single phase liquid medium and does not involve the formation of the two phase emulsions observed in conventional, mixed sulfuric/nitric acid nitration processes. Another surprising aspect of this invention is that the reaction can be conducted under moderate reaction conditions to provide an excellent yield of the desired mononitrobenzene or dinitrobenzene product.

When a mononitrobenzene product is desired, the reaction is suitably conducted at a reaction temperature not exceeding 80° C., preferably between 0° C. and 60° C., more preferably between 10° C. and 60° C. The reaction is suitably conducted at a pressure not exceeding atmospheric pressure, preferably at atmospheric pressure or under a slight vacuum, although superatmospheric pressure can be employed if desired for some purpose. The reaction time to form mononitrobenzene is typically less than one-half hour, preferably less than 15 minutes, and more preferably less than 5 minutes.

The process for producing dinitrobenzene is suitably conducted at a reaction temperature of between about 30° C. and about 70° C., preferably between about 50° C. and about 70° C., more preferably about 65° C. The reaction is suitably conducted at a pressure not exceeding atmospheric pressure, preferably at atmospheric pressure or under a slight vacuum, although superatmospheric pressure can be employed if desired for some purpose. The reaction time to form dinitrobenzene is preferably less than two hours, preferably less than one-half hour.

For the reaction of benzene to dinitrobenzene, the molar ratio of nitric acid plus water to benzene employed is between 15:1 and 25:1, preferably between 15:1 and 20:1. For the reaction of benzene to mononitrobenzene, the molar ratio of nitric acid plus water to benzene employed is between 2:1 and 4:1, preferably between 2.5:1 and 3.5:1. Operating within the above-recited broad ranges of molar ratios (and particularly within the preferred ranges) maximizes the production of the desired product and minimizes by-product formation.

After reaction and product formation, it is desired that excess (unreacted) nitric acid be removed from the reactor, preferably by vacuum distillation, thus providing a low temperature, low pressure distillation. Suitable distillation temperatures range from 30° C. to 60° C. Suitable distillation pressures range from 50 mm of Hg to 300 mm of Hg.

Following removal of the excess anhydrous nitric acid, mononitrobenzene or dinitorbenzene separation from the distillation still bottoms can be effected by phase separation, brought about by the addition of a small quantity of water or dilute nitric acid. Washing with water and a basic solution produces a purified monitrobenzene or dinitrobenzene product. These wash waters are free of the mononitro- and dinitro-cresol impurities observed in the wastewater produced in a conventional, mixed sulfuric/nitric acid DNT process. The aqueous nitric acid from the phase separation step can be purified by benzene extraction, the benzene phase being recycled to the reaction step and the 60–70% aqueous nitric acid phase reconcentrated, sold or used in other product manufacture.

The following examples are intended to illustrate, but in no way limit the scope of, the present invention.

EXAMPLE 1

Synthesis of Mononitrobenzene

A four milliliter glass vial, equipped with a magnetic stir bar and a silicone septum, was immersed in a water bath. The reaction vial was flushed with nitrogen at a rate of 20 cc/min, purging to a 100 ml glass receiving flask immersed in an ice water bath. To the reaction vial was fed 7.0 ml of 98 percent $HNO_3$, 10.5 g, 0.163 mole of $HNO_3$ and 5.0 ml, 4.39 g, 0.056 mole of benzene. The feed rates were 0.22 ml/min and 0.135 ml/min into the reaction vial for the nitric acid and the benzene, respectively, and these feed rates were controlled by Sage Instrument syringe pumps, Models 351 and 355. The reactor content was adjusted to 2 ml, by height adjustment of the reactor exit line in the reaction vial, for a mean reaction residence time of 2.8 minutes. The reactor water bath was maintained at 15 degrees Centigrade (plus or minus 5 degrees) by the periodic addition of ice during the reactants addition. Upon completion of the reactants addition, the contents of the reactor were stirred for three minutes, and then purged to the reciver. A pale yellow product solution was obtained in an amount of 14.65 g of pale yellow product solution was diluted with 42.49 g of ice water and extracted with 2×15 ml of methylene chloride. Dilute acid recovery was 51.39 g, for an organic recovery of 5.75 g, by difference. Gas chromatographic analysis of the organic product showed only nitrobenzene, exclusive of the methylene chloride solvent peak, for a recovery of 0.047 mole (83 percent) of nitrobenzene. $HNO_3$ accountability, as recovered weak acid and nitrobenzene equivalent, was 96 percent.

EXAMPLE 2

Benzene Dinitration

A magnetically stirred solution of 55.07 g (0.857 mole) of 98% nitric acid in a 100 ml flask was chilled in a water bath. Benzene (3.71 g, 0.048 mole) was injected subsurface to the nitric acid at 0.75 ml/min with a Sage Instrument Model 355 syringe pump. Ice was periodically added to the water bath to maintain a reaction temperature of not greater than 65° C. Periodically, one-half milliliter sample aliquots were taken, quenched with ice water, extracted with methylene chloride, the methylene chloride layer dried over magnesium sulfate, and the resulting organic solution analyzed by gas chromatography. Complete conversion (mononitrobenzene content of less than 200 ppm) occurred in less than one hour. Trinitrophenol content (hexadecane internal standard gas chromatographic calibration) was estimated at 200 ppm in the crude dinitrobenzene product. The results from other reaction conditions are shown in the table below. Trinitrophenol content (an undesirable byproduct from a waste treatment point of view) is clearly controllable by the proper selection of reaction conditions, with a molar ratio of nitric acid to benzene of 18:1 being particularly advantageous for the dinitration reaction.

| BENZENE DINITRATION BATCH REACTION | | | | | | |
|---|---|---|---|---|---|---|
| | | | Product Isomers | | | |
| Ratio[a] | °C. | Time, Hr[b] | 1,2 | 1,3 | 1,4 | ppm Phenols[c] |
| 18:1 | 30 | 20 | 9.0 | 89.6 | 1.4 | — |
| 18:1 | 50 | 3 | 9.6 | 88.5 | 1.9 | 780 |
| 18:1 | 65 | <1 | 9.6 | 88.3 | 2.0 | 200 |
| 12:1 | 65 | 5 | 9.9 | 87.8 | 2.2 | 3120 |

[a]Mole ratio of 98% $HNO_3$ plus water to benzene
[b]Reaction time to less than 200 ppm nitrobenzene
[c]Internal standard gas chromatographic calibration for trinitrophenols. Mono- and dinitrophenols not detected in the final crude product.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for nitrating benzene to produce dinitrobenzene by a liquid phase nitration reaction of anhydrous nitric acid with benzene in a reactor at a reaction temperature of between 30° C. and 70° C., and a reaction pressure not exceeding atmospheric pressure, said reaction employing a molar ratio of nitric acid plus any water to benzene of between 15:1 and 25:1, said reaction being conducted in the absence of sulfuric acid, and in the absence of any aprotic dipolar solvent during the reaction and in the absence of any aprotic dipolar solvent to halt the reaction, to produce said dinitrobenzene in a product mixture, followed by vacuum distillation of the product mixture, in the absence of any aprotic dipolar solvent, to remove unreacted nitric acid from said product mixture thereby providing a dinitrobenzene product.

2. The process of claim 1 wherein said anhydrous nitric acid has an acid content of between 95 percent and 100 percent by weight based upon the acid plus water therein.

3. The process of claim 1 wherein said vacuum distillation is effected at a temperature of between about 30° C. and about 60° C.

4. The process of claim 1 wherein said vacuum distillation is effected at a pressure of between about 50 mm of Hg and about 300 mm of Hg.

5. The process of claim 1 which additionally comprises, after said vacuum distillation, phase separation of dinitrobenzene from said product mixture.

6. The process of claim 5 wherein said phase separation is caused by the addition of water or dilute nitric acid to said product mixture.

7. The process of claim 1 wherein said nitration reaction is conducted at a reaction temperature of between 50° C. and 70° C.

8. The process of claim 1 wherein said nitration reaction is conducted for a reaction time of less than about two hours.

9. The process of claim 1 wherein said nitration reaction is effected in between one-half hour and two hours.

10. The process of claim 1 which additionally comprises, after said vacuum distillation, phase separation of mononitrobenzene from said product mixture.

11. The process of claim 10 wherein said phase separation is caused by the addition of water or dilute nitric acid to said product mixture.

12. The dinitrobenzene produced by the process of claim 1 which is free of mononitro- and dinitro-phenol species.

* * * * *